(12) United States Patent
Choi et al.

(10) Patent No.: US 8,982,355 B2
(45) Date of Patent: Mar. 17, 2015

(54) SMART OPTICAL MATERIAL CHARACTERIZATION SYSTEM AND METHOD

(75) Inventors: Sang Hyouk Choi, Poquoson, VA (US); Yeonjoon Park, Yorktown, VA (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 184 days.

(21) Appl. No.: 12/964,381

(22) Filed: Dec. 9, 2010

(65) Prior Publication Data

US 2012/0147379 A1 Jun. 14, 2012

(51) Int. Cl.
| | |
|---|---|
| *G01J 3/45* | (2006.01) |
| *G01B 9/02* | (2006.01) |
| *G01B 11/02* | (2006.01) |
| *G01N 21/41* | (2006.01) |
| *G01J 9/02* | (2006.01) |
| *G01N 21/21* | (2006.01) |
| *G01N 21/45* | (2006.01) |

(52) U.S. Cl.
CPC . *G01J 9/02* (2013.01); *G01N 21/21* (2013.01); *G01N 21/45* (2013.01)
USPC ............ 356/451; 356/481; 356/515; 356/517

(58) Field of Classification Search
USPC ......... 356/450, 451, 453, 456, 491, 495, 517, 356/515, 481
See application file for complete search history.

(56) References Cited

U.S. PATENT DOCUMENTS

| | | | | |
|---|---|---|---|---|
| 4,950,074 A | * | 8/1990 | Fabricius et al. | 356/133 |
| 5,011,280 A | * | 4/1991 | Hung | 356/35.5 |

(Continued)

FOREIGN PATENT DOCUMENTS

WO 0104569 A1 1/2001

OTHER PUBLICATIONS

Yeonjoon Park, Sangjoon Park, Uhn Lee, Kunik Lee, Sang Choi, "Versatile Smart Optical Material Characterization System", Nanosensors, Biosensors, and Info-Tech Sensors and Systems 2010, edited by Vijay K. Varadan, Proc. of SPIE vol. 7646, 764613, 2010 SPIE.

(Continued)

*Primary Examiner* — Kara E Geisel
*Assistant Examiner* — Hina F Ayub
(74) *Attorney, Agent, or Firm* — Jennifer L. Riley; Thomas K. McBride

(57) ABSTRACT

Disclosed is a system and method for characterizing optical materials, using steps and equipment for generating a coherent laser light, filtering the light to remove high order spatial components, collecting the filtered light and forming a parallel light beam, splitting the parallel beam into a first direction and a second direction wherein the parallel beam travelling in the second direction travels toward the material sample so that the parallel beam passes through the sample, applying various physical quantities to the sample, reflecting the beam travelling in the first direction to produce a first reflected beam, reflecting the beam that passes through the sample to produce a second reflected beam that travels back through the sample, combining the second reflected beam after it travels back though the sample with the first reflected beam, sensing the light beam produced by combining the first and second reflected beams, and processing the sensed beam to determine sample characteristics and properties.

20 Claims, 17 Drawing Sheets

(56) References Cited

U.S. PATENT DOCUMENTS

| | | | | |
|---|---|---|---|---|
| 5,483,344 | A * | 1/1996 | Frot et al. | 356/484 |
| 6,128,081 | A | 10/2000 | White et al. | |
| 6,515,750 | B1 * | 2/2003 | Malyak et al. | 356/512 |
| 6,744,517 | B1 * | 6/2004 | Forno et al. | 356/450 |
| 6,753,968 | B2 * | 6/2004 | Hill | 356/491 |
| 7,006,234 | B1 * | 2/2006 | Cottrell et al. | 356/515 |
| 7,046,373 | B2 * | 5/2006 | Coppola et al. | 356/517 |
| 7,551,293 | B2 * | 6/2009 | Yelin et al. | 356/497 |
| 7,835,013 | B2 * | 11/2010 | Jones et al. | 356/517 |
| 7,876,450 | B2 * | 1/2011 | Novotny et al. | 356/491 |
| 8,164,756 | B2 * | 4/2012 | Arvidson et al. | 356/450 |
| 2005/0231733 | A1 * | 10/2005 | Pfaff et al. | 356/517 |
| 2006/0098204 | A1 * | 5/2006 | Kenda et al. | 356/450 |
| 2006/0181714 | A1 | 8/2006 | Mater et al. | |
| 2007/0086017 | A1 * | 4/2007 | Buckland et al. | 356/497 |
| 2009/0116033 | A1 * | 5/2009 | Wang et al. | 356/481 |
| 2010/0103403 | A1 * | 4/2010 | Ishizuka | 355/77 |
| 2010/0238455 | A1 * | 9/2010 | de Groot | 356/512 |
| 2010/0290055 | A1 * | 11/2010 | Kim et al. | 356/453 |
| 2011/0102803 | A1 * | 5/2011 | Wang et al. | 356/480 |
| 2011/0170108 | A1 * | 7/2011 | Degertekin | 356/454 |
| 2011/0292394 | A1 * | 12/2011 | Wu et al. | 356/451 |
| 2012/0176627 | A1 * | 7/2012 | Weinberger et al. | 356/517 |

OTHER PUBLICATIONS

Rene M. de Ridder. Alfred Driessen, Erwin Rikkers, Paul V. Lambeck Mart B.J. Diemeer, "Design and fabrication of electro-optic polymer modulators and switches", Optical Materials 12 (1999) 205-214.

A. Balbin Villaverde, D. A. Donatti, D. G. Bozinis, "Terbium gallium garnet Verdet constant measurements with pulsed magnetic field", J. Phys. C: Solid State Phys., vol. 11, 1978. Printed in Great Britain 1978.

M.A. Jeppesen and A. M. Taylor, "Thickness and Refractive Index Measurement of a Lamina with a Michelson Interferometer", Journal of the Optical Society of America, vol. 56, No. 4, Apr. 1966.

* cited by examiner

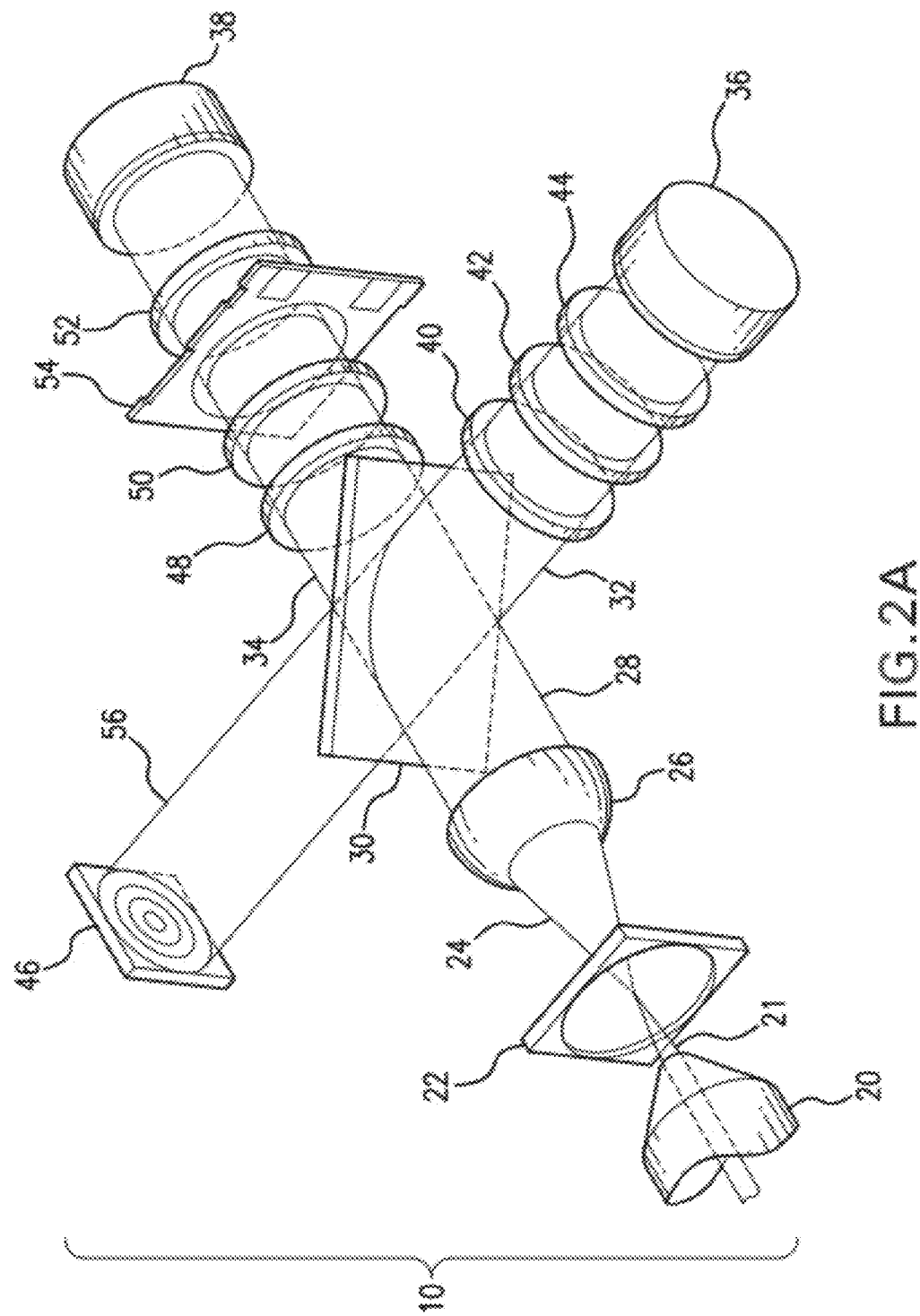

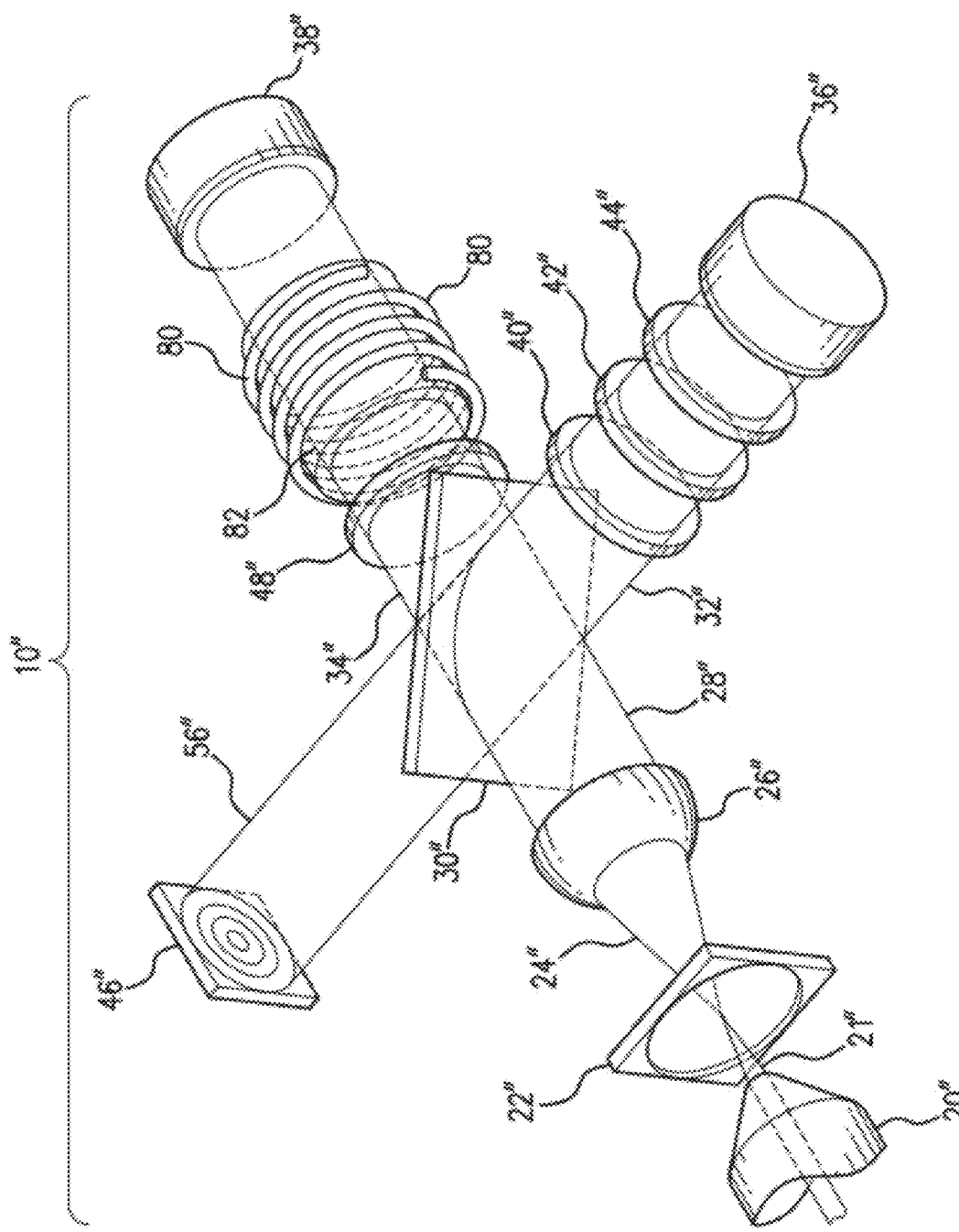

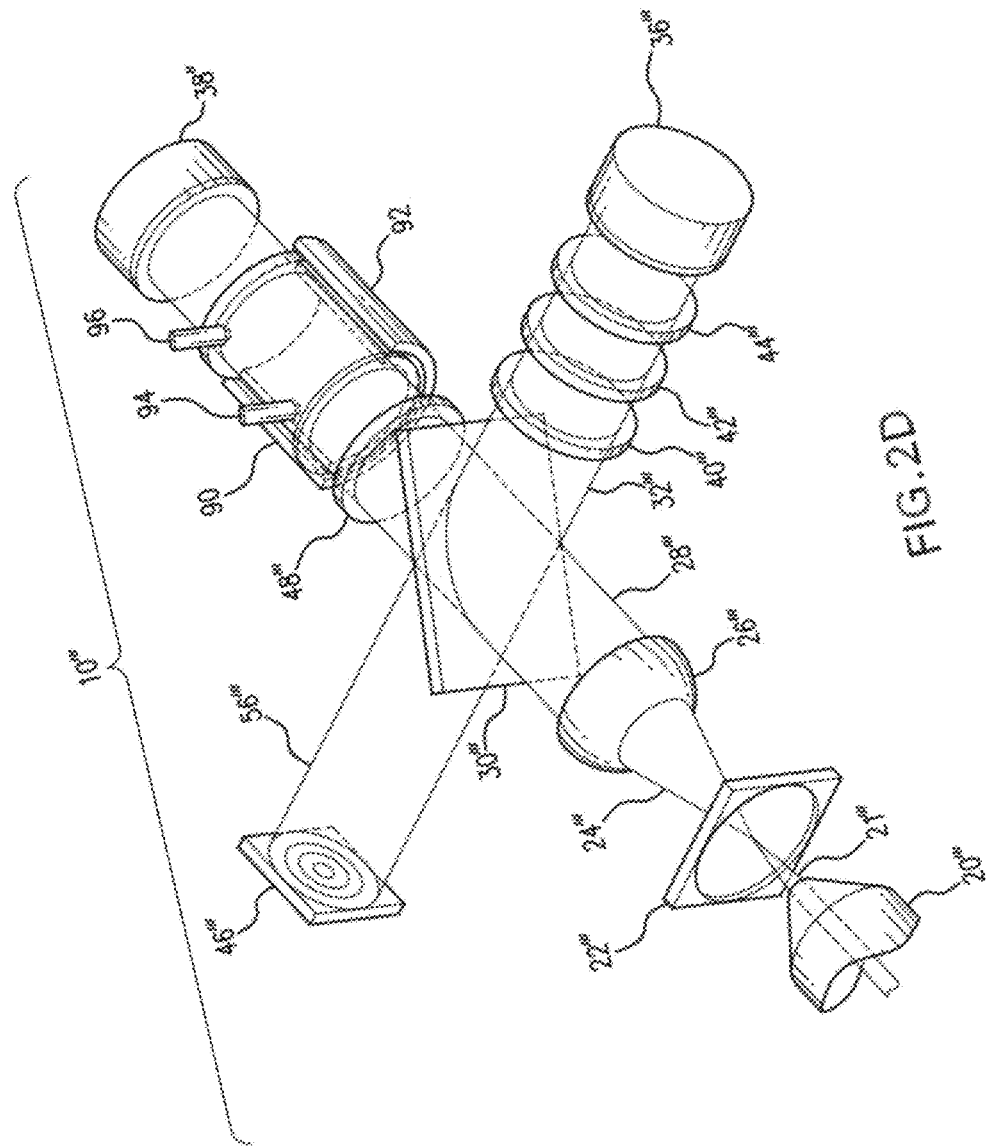

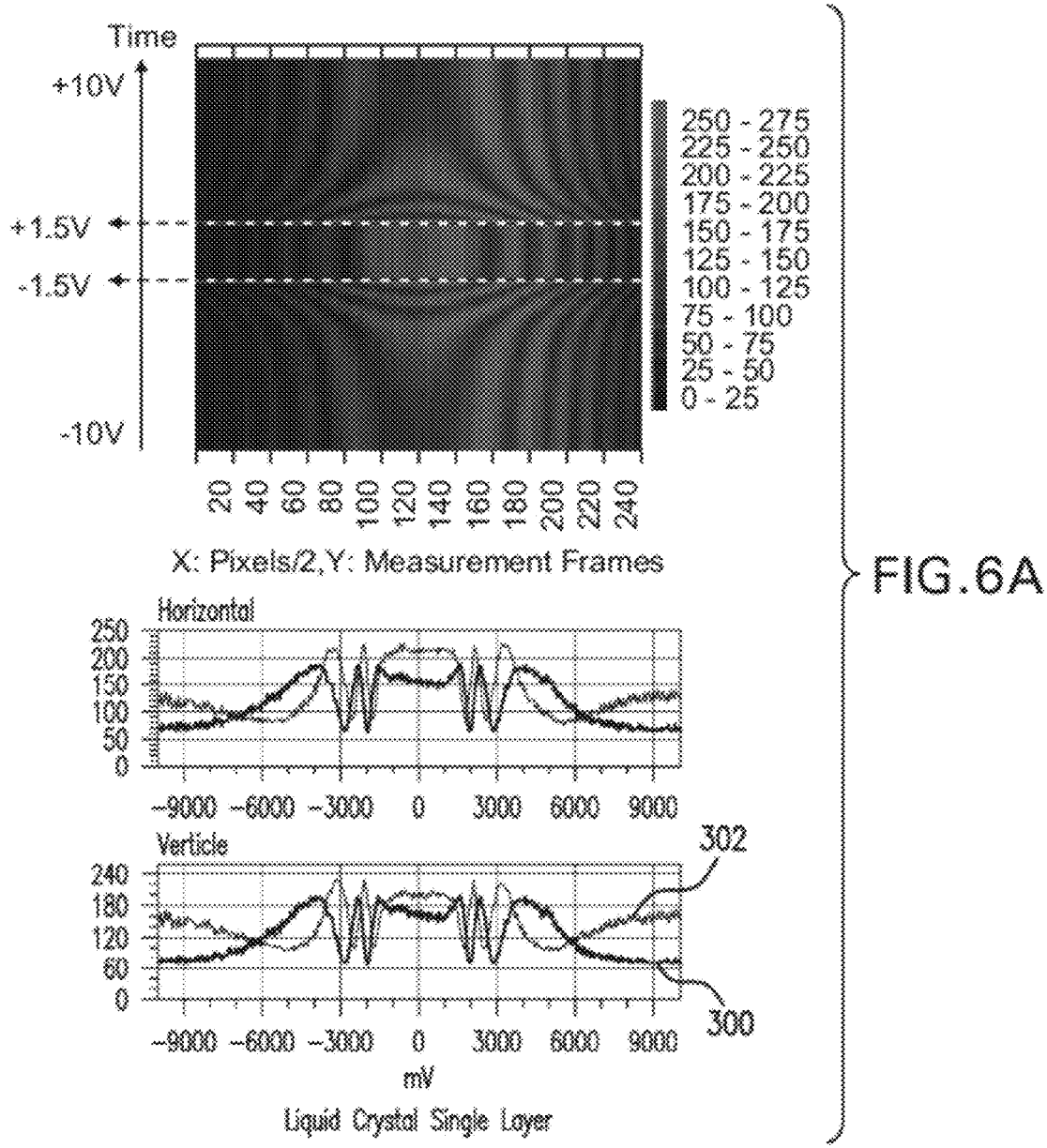

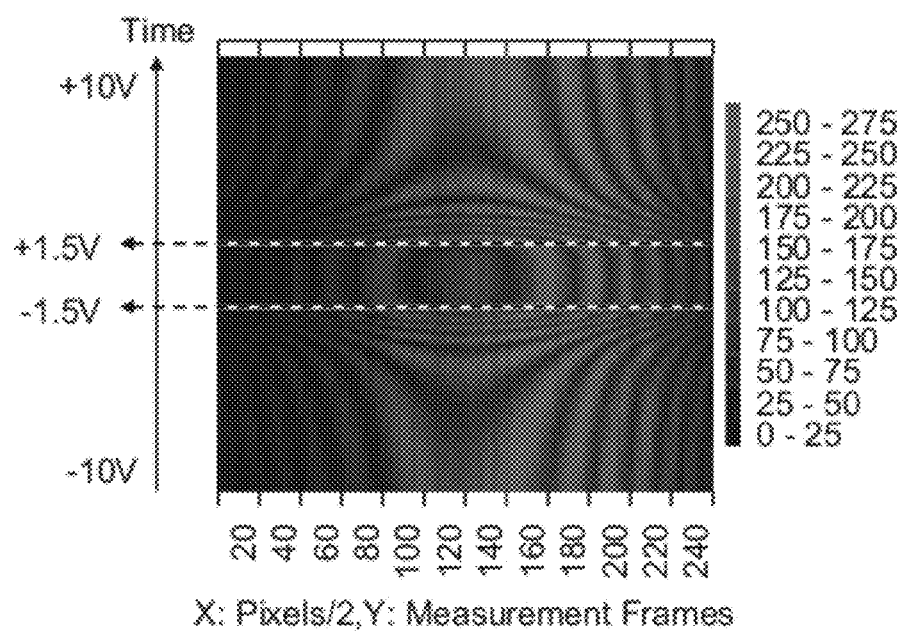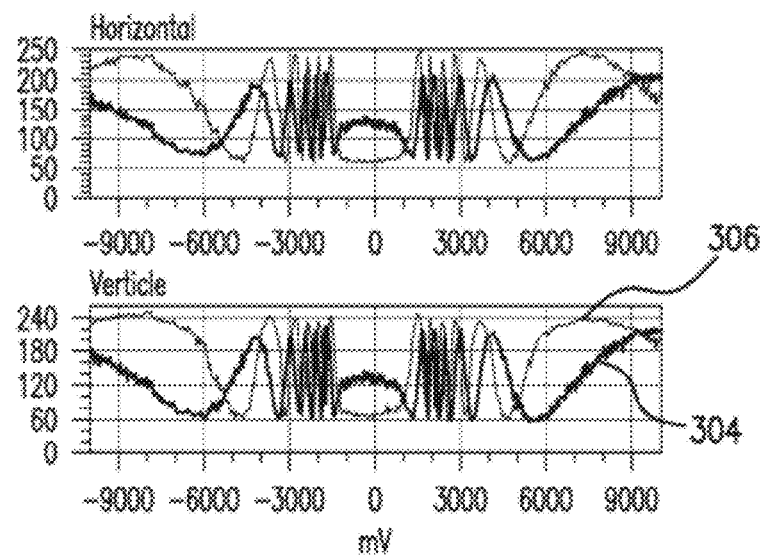
FIG.6B

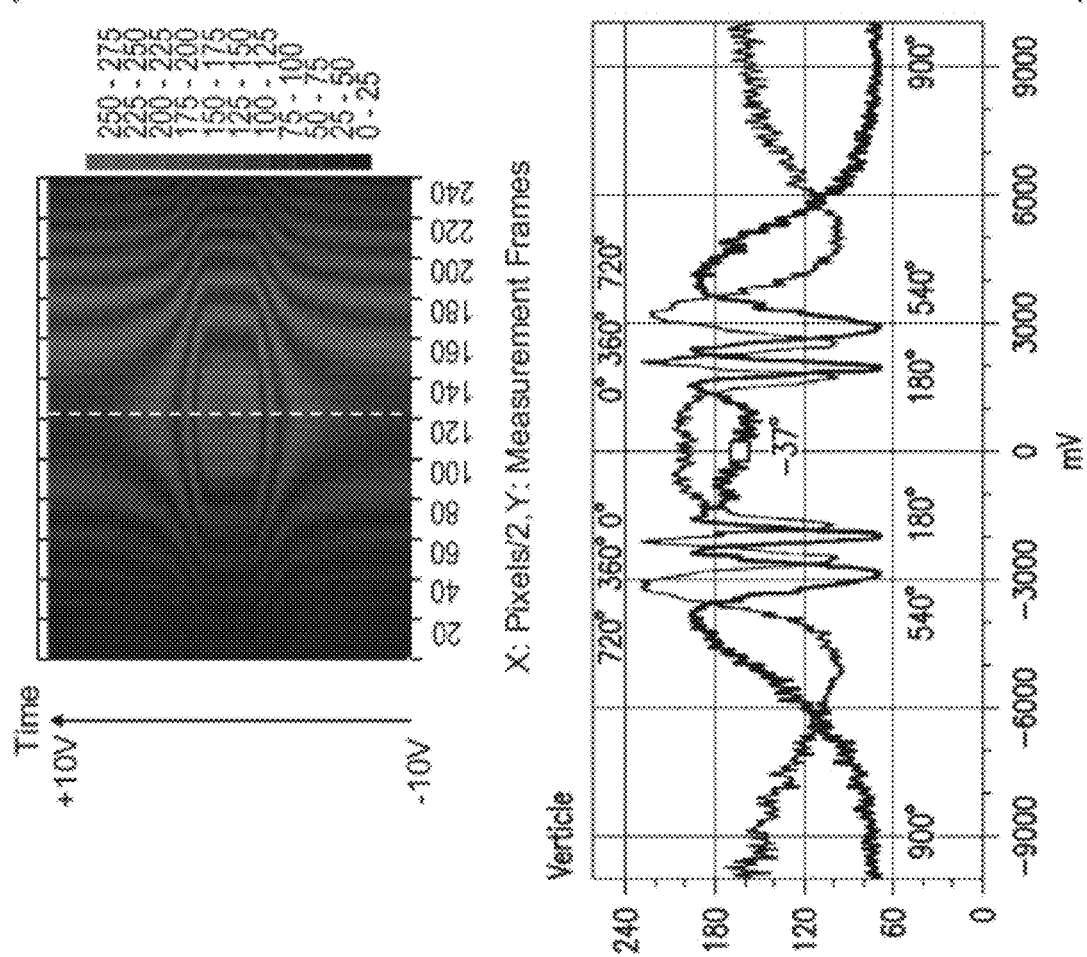

SMART OPTICAL MATERIAL CHARACTERIZATION SYSTEM AND METHOD

ORIGIN OF THE INVENTION

The invention was made in part by employees of the United States Government and may be manufactured and used by or for the Government of the United States of America for governmental purposes without the payment of any royalties thereon or therefore.

BACKGROUND OF THE INVENTION

Smart Optical Materials ("SOM") are optical materials that can control deep properties such as, for instance, intensity, phase, polarization, and/or coherence of passing lights. SOM include electro-optic materials, non-linear optical crystals, liquid crystals, electro-optic polymers, magneto-optic materials (Faraday Effect and Kerr Effect), electro/thereto-chromic materials, chemicals that induce refractive index or optical density changes, optical materials that depend on temperature and pressure, and phase-change materials. For example, liquid crystal material has different refractive indices under an electric field. In another example, non-linear optical crystal ($BaTiO_3$) material has a dipole moment and electric field that affects domains of similar dipole moments which change the total index of refraction. Characterization of these SOM appears difficult due to the lack of standard methods and commercially available equipment that can measure the intensity, phase of photons and its related polarization. Furthermore, the characterization of the properties of some optical materials ordinarily requires many separate, stand-alone pieces of equipment that make moving samples of optical material from one station to another quite cumbersome. Such a station-to-station characterization process imposes unprotected vulnerability to samples due to the exposure to moisture, dust, and environment-enhanced aging effects.

BRIEF SUMMARY OF THE INVENTION

In view of the foregoing, it is an object of the invention to provide a system and method for characterizing smart optical materials to determine spectral and refractive shifts in terms of deep properties (e.g. intensity, phase, polarization, coherence) of passing lights.

It is a related object of the invention to provide the ability to characterize smart optical materials in a compact, economical and efficient way.

These objects are achieved by the present invention, which provides a system and a method for characterizing smart optical materials that can simultaneously measure intensity, phase and polarization of photons passing through the material. The present invention measures intensity, phase, and polarization of passing lights through material while applying various physical and/or chemical quantities (such as voltage, electric field, current, magnetic field, chemical concentration, temperature, pressure, reaction time, etc.) on the material. In a preferred embodiment, the system is miniaturized and comprises a USB interface and exchangeable components for various applications. Such a system can be used as a complete micro spectrometer system.

In one aspect, the invention provides a method for characterizing optical materials, comprising the steps of providing a sample of optical material, generating a coherent laser light, filtering the coherent laser light in order to remove high order spatial components of laser light, collecting the filtered light and forming a parallel beam of light, splitting the parallel beam of light into a first direction and into second direction toward the sample of optical material so that the parallel beam of light passes through the optical material, applying physical quantities to the sample of optical material, reflecting the beam of light travelling in the first direction to produce a first reflected beam of light, reflecting the beam of light that passes through the optical material to produce a second reflected beam of light that travels back through the optical material, combining the second reflected beam of light after it travels back though the optical material with the first reflected beam of light, sensing the light beam produced by combining the first and second reflected beams of light, and processing the sensed light beam to determine the optical characteristics and properties of the sample of optical material.

In another aspect, the invention provides a system for characterizing optical materials including a sample holder for holding a sample of optical material, a laser to generate a coherent laser light, a filter for filtering the coherent laser light in order to remove high order spatial components of laser light, an optical device to collect the filtered light and form a parallel beam of light, an optical beam splitter to split the parallel beam of light into a first direction and into second direction wherein the parallel beam of light travelling in the second direction travels toward the sample holder so that the parallel beam of light passes through the sample of optical material secured within the sample holder, a means for applying physical quantities to the sample of optical material, a first optical reflector to reflect the beam of light travelling in the first direction to produce a first reflected beam of light, a second optical reflector to reflect the beam of light that passes through the optical material to produce a second reflected beam of light that travels back through the optical material, a light combining device to combine the second reflected beam of light after it travels back though the optical material with the first reflected beam of light, an imaging sensor to sense the light beam produced by combining the first and second reflected beams of light; and a processing resource to process the sensed light beam to determine the optical characteristics and properties of the sample of optical material.

Additional objects, embodiments and details of this invention can be obtained from the following detailed description of the invention.

BRIEF DESCRIPTION OF THE SEVERAL VIEWS OF THE DRAWING(S)

FIG. 2A is a perspective view of the smart optical material characterization system of FIG. 1 utilizing a sample holder configured to hold electro-optical materials;

FIG. 2C is a perspective view of a smart optical material characterization system in accordance with a further embodiment that of the present invention that utilizes a sample holder configured to hold magneto-optical materials;

FIG. 2D is a perspective view of a smart optical material characterization system in accordance with yet another embodiment of the present invention that utilizes a sample holder configured to hold chemical-optical materials;

FIG. 6A shows a phase intensity time ripple map and a point intensity measurement graph generated by the system of the present invention for a single layer of liquid crystal cell;

FIG. 6B shows a phase intensity time ripple map and a point intensity measurement graph generated by the system of the present invention for a double layer of liquid crystal cell;

FIG. 7 shows the phase measurement result of the point intensity chart; and

DETAILED DESCRIPTION OF THE INVENTION

Figure 1:
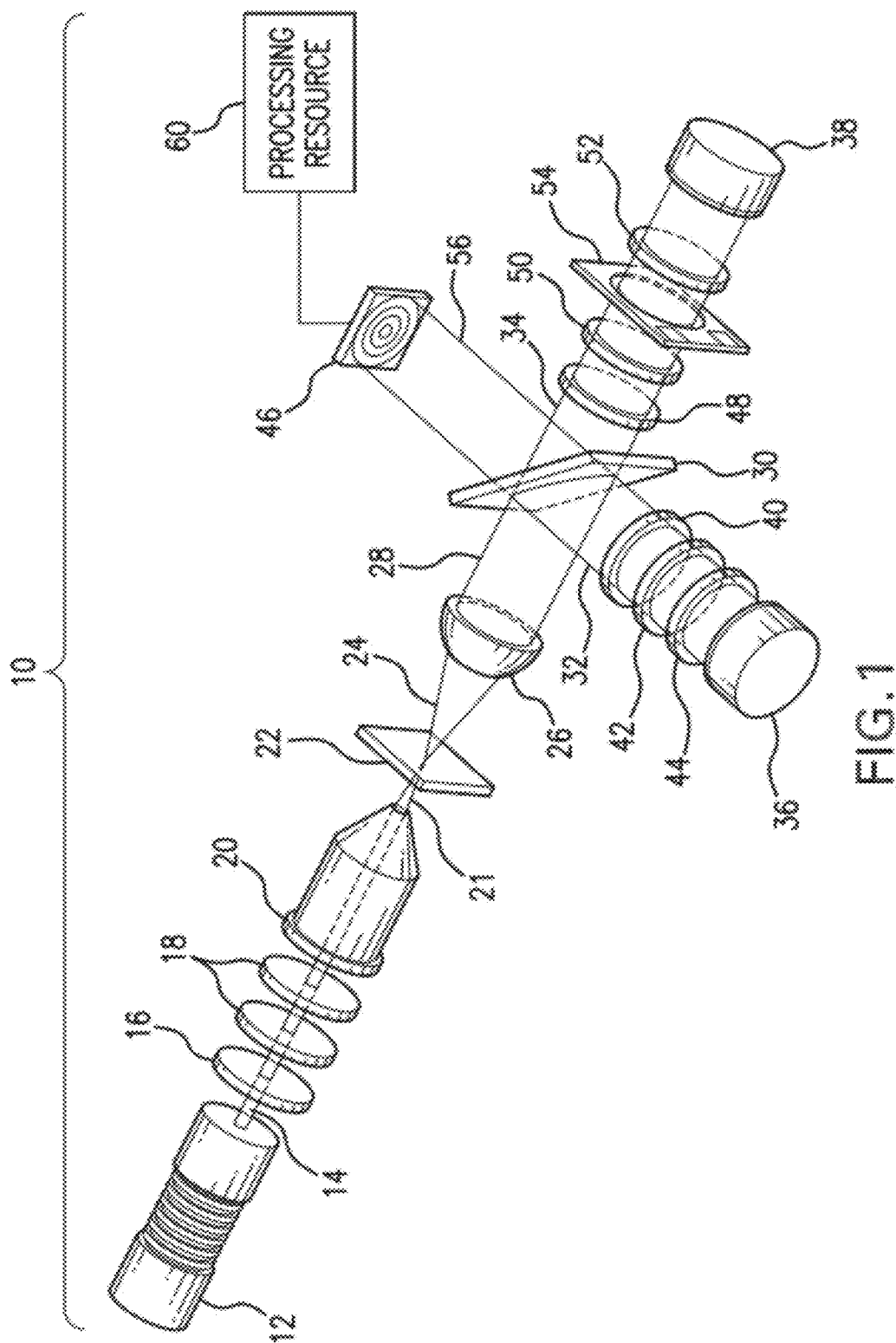
FIG. 1 is a perspective view of the smart optical material characterization system of the present invention.

Referring to FIG. 1, there is shown system 10 of the present invention. System 10 employs a Michelson interferometer which uses a 45° inclined beam splitter, two mirrors, and a screen with a coherent light source such as a laser. An interference pattern is produced from two splitted lights reflected by two mirrors. The Michelson interferometer configuration is well known in the art and therefore, is not discussed in detail herein. System 10 further comprises several other optical components and a processing resource that are discussed in detail in the ensuing description. Laser source 12 generates coherent laser light 14 beam. In a preferred embodiment, system 10 includes a polarizer 16, wave plates 18, and neutral density (ND) filter 20. The wave plate (also known as a retarder) alters the polarization state of a light wave travelling through it. In one embodiment, there is a plurality of wave plates 18. Neutral density filter 20 achieves the desired light attenuation without changing the other properties of the laser light 14. Laser light 14 passes through neutral density filter 20 and becomes altered laser light 21. Laser light 21 passes through spatial filter 22 which removes high-order spatial components from laser light beam 21 and provides a uniform $TEM_{00}$ mode light beam 24. Plano-convex (PCX) lens 26 collects diverging laser light beam 24 from spatial filter 22 and provides parallel $TEM_{00}$ beam 28. Beam splitter 30 divides beam 28 into two different laser light beams 32 and 34 that travel toward mirrors 36 and 38, respectively. Beam splitter 30 can be configured as a polarizing or non-polarizing beam splitter depending on the measurement necessity. Polarizer 40, wave plate 42 and neutral density (ND) filter 44 modify or alter laser light beam 32 in order to provide an excellent, high contrast, interference pattern for imaging sensor 46. Similarly, polarizer 48, wave plate 50 and neutral density (ND) filter 52 modify or alter laser light beam 34 to provide an excellent, high contrast, interference pattern for imaging sensor 46. System 10 includes a Smart Optical Material (SOM) sample holder 54 that holds therein a sample of Smart Optical Material. Straight beam 34 travels through sample holder 54 and neutral density filter 52 and then reflected backward from mirror 38. Therefore, beam 34 travels through sample holder 54 twice, once in the forward direction and once in the backward or reflected direction. Beam 32 is reflected back from mirror 36. The reflected beams are recombined at beam splitter 30 to form laser light beam 56 which travels toward imaging sensor 46. In a preferred embodiment, there are no other optical components between beam splitter 30 and imaging sensor 46. In such an embodiment, laser light beam 56 directly illuminates imaging sensor 46. Imaging sensor 46 comprises an imaging device to capture the interference patterns of laser light 56. In one embodiment, imaging sensor 46 is configured as a CCD or NMOS-type imaging sensor. In another embodiment, imaging sensor 46 comprises screen and video camera imaging module that measures the two-dimensional interference pattern. Processing resource 60 is in electrical and optical communication with imaging sensor 46 and processes the interference patterns captured by imaging sensor 46. Processing resource 60 includes a microprocessor, optical measurement components, optical analysis components, and a display device. In one embodiment, processing resource 60 includes a computer that is configured to implement software that performs analysis on the images and interference patterns detected by imaging sensor 46. In some embodiments, the system is miniaturized and comprises a USB interface (not shown).

In accordance with the invention, system 10 applies physical quantities on sample holder 54 and measures the dynamic change of the interference pattern in sequence. The variable physical quantities include voltage (electric field), current, magnetic field, chemical concentration (i.e. chemical density and/or reaction time), temperature, pressure, and actuation frequency. Thus, it is to be understood that system 10 includes devices (not shown) such as variable voltage sources and variable current sources that are used to apply a voltage or electrical current to the SOM under test. System 10 also includes devices (not shown) to provide an actuation frequency that is applied to the SOM under test. Similarly, system 10 also may include other devices (not shown) to provide a predetermined pressure that is applied to the SOM under test. As described below, system 10 enables various types of measurements with different sample holders. The sample holders and optical components are exchangeable parts with mountable slots and screws. Referring to FIGS. 2A-D and 3A-3H, there are shown various types of sample holder and optical components for each measurement. FIG.

Figure 2B:
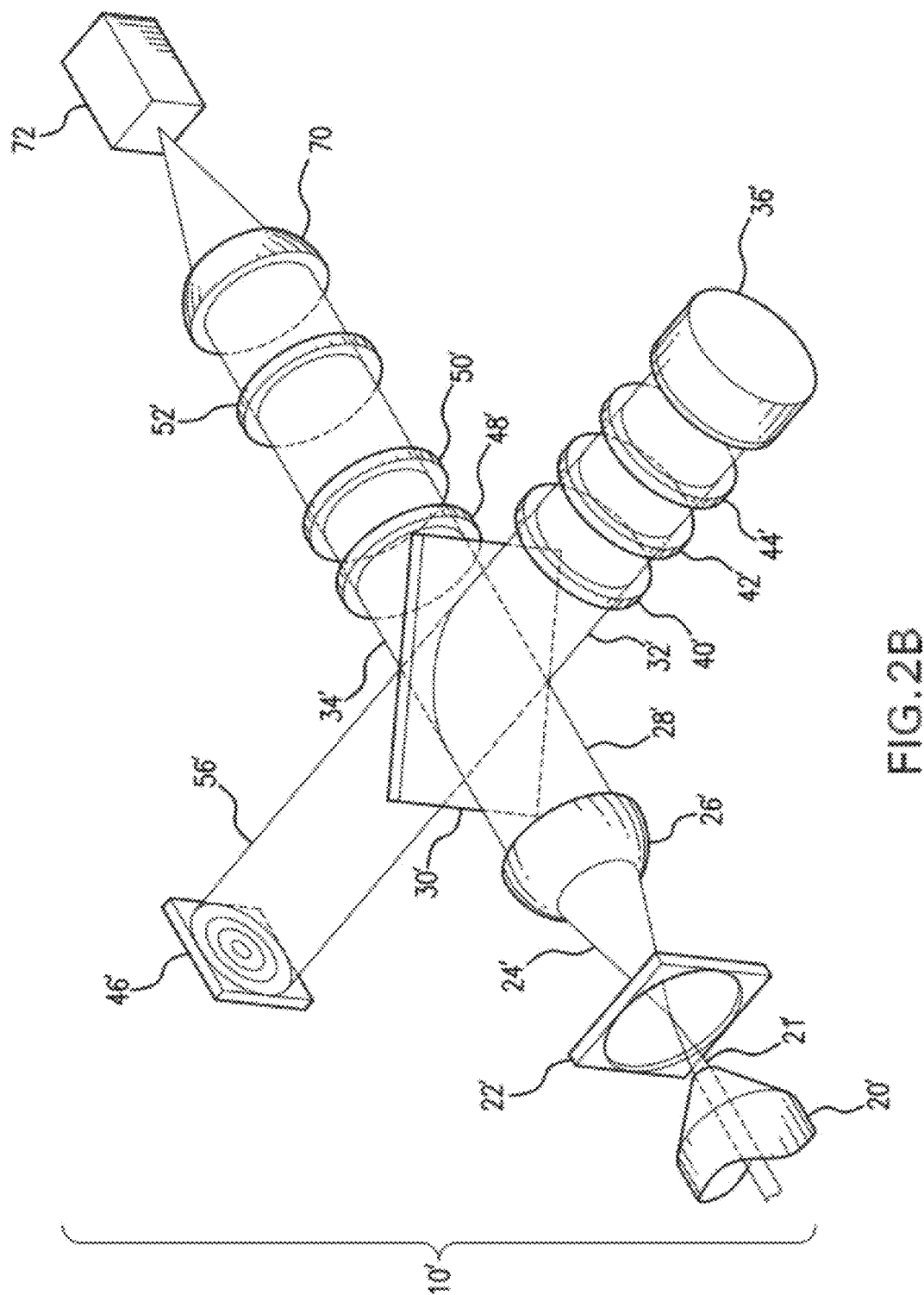
FIG. 2B is a perspective view of a smart optical material characterization system in accordance with another embodiment of the present invention that is configured to test a sample of reflective material.

2A shows the configuration for electro-optic measurement, i.e. voltage/current versus optical properties such as phase, intensity, polarization, coherence, etc. This is also the configuration shown in FIG. 1. FIGS. 2B and 3E show system 10' for reflective measurement for MEMS devices, piezoelectric actuator materials, thermal coefficient measurements, and stress/strain measurement. Reflective measurement is accomplished with focusing and collection lens 70 and reflective sample holder 72. Optical material 73 is secured by the sample holder 72 and has a reflective or diffusive surface. Laser light 75 is reflected from surface 74 and is collected with the focusing and collection lens 70. Beam splitter 30' directs the collected, reflective light to imaging sensor 46'. System 10' is a particularly preferred method to characterize MEMS device movement, piezoelectric actuator materials, thermal expansion, and stress/strain measurement. An optional heater/refrigerator and pressure cell can be used to control temperature or pressure dependent properties. FIGS. 2C and 3F show system 10" which is configured for magneto-optical measurement, i.e. magnetic materials with Faraday effect, Kerr effect, Ferro-fluid, etc. System 10" uses a magneto-optical sample holder which comprises induction coil 80 that surrounds the optical material 82. Induction coil 80 generates a magnetic field along the propagation direction of the laser light. FIG. 3G shows an alternate magneto-optical sample holder 85. Sample holder 85 comprises permanent magnet 86. Optical material 87 is positioned between sections 86A and 86B of permanent magnet 86. A perpendicular magnetic field is generated by permanent magnet 86. Both sample holders 80 and 85 can be fabricated with a permanent magnet or electric magnet. Magneto-optical sample holders 80 and 85 are used to characterize ferromagnetic fluid and magnetic materials with Faraday Effect or Kerr Effect.

Figure 3A:
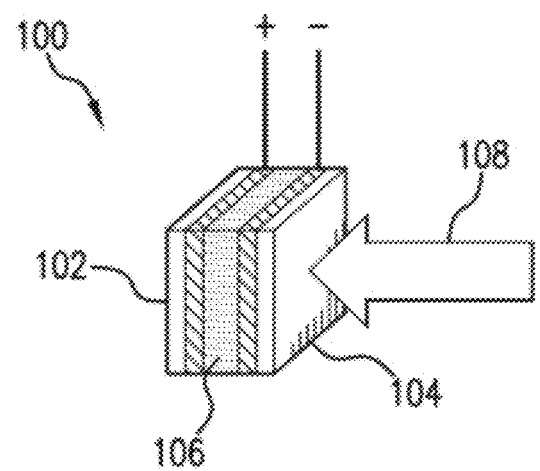
FIG. 3A is a perspective view of a sample holder configured to hold an electro-optical material in accordance with one embodiment of the present invention.
Figure 3B:
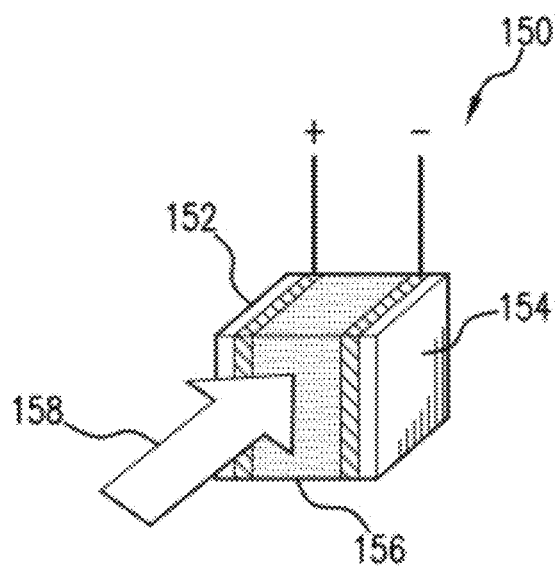
FIG. 3B is a perspective view of a sample holder configured to hold an electro-optical material in accordance with another embodiment of the present invention.
Figure 3C:
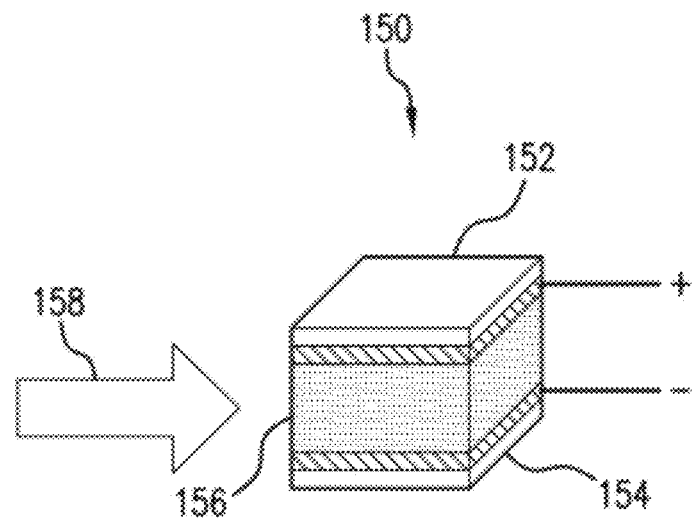
FIG. 3C is a perspective view of a sample holder configured to hold an electro-optical material in accordance with a further embodiment of the present invention.
Figure 3D:
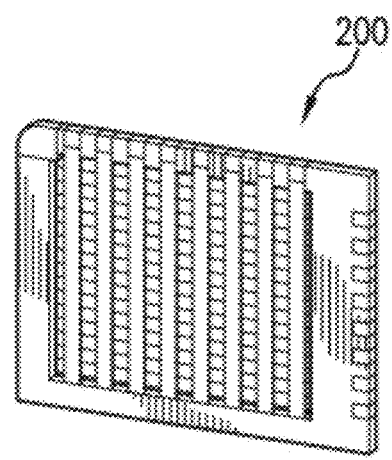
FIG. 3D is a perspective view of a sample holder configured as a two-dimensional array in accordance with yet another embodiment of the present invention.
Figure 3E:
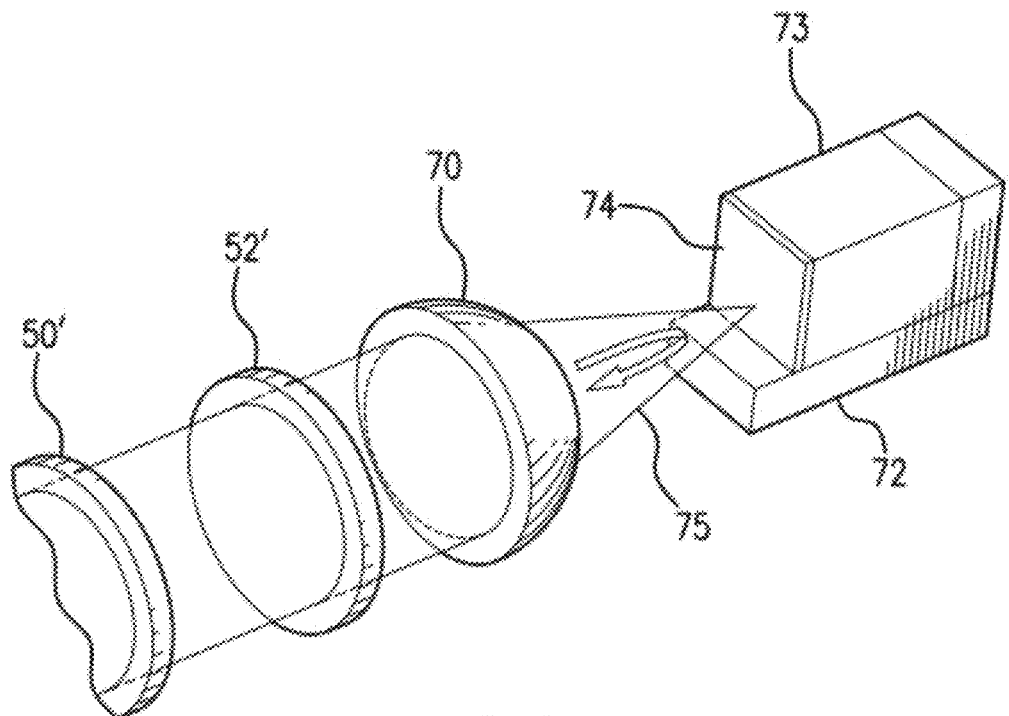
FIG. 3E is a perspective view of a sample holder for a reflective material in accordance with yet a further embodiment of the present invention.
Figure 3F:
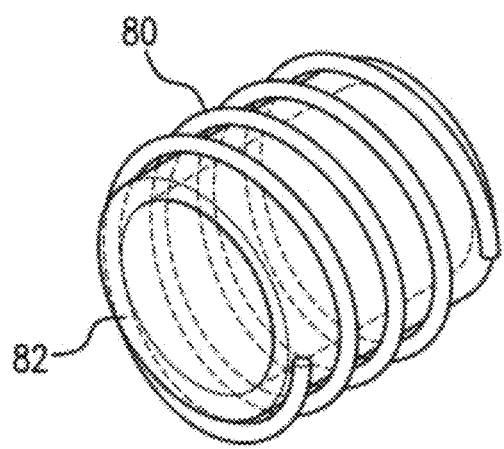
FIG. 3F is a perspective view of a sample holder configured as an inductive coil for holding a magneto-optical material in accordance with yet another embodiment of the present invention.
Figure 3G:
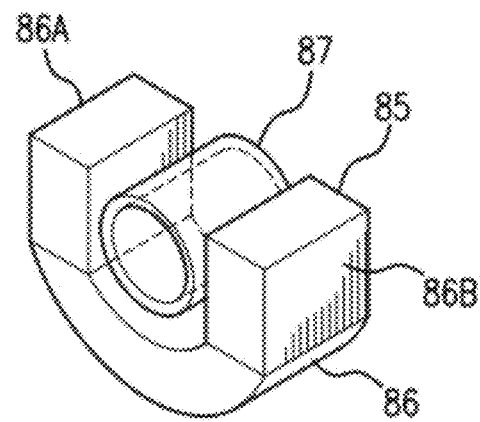
FIG. 3G is a perspective view of a sample holder configured as a magnet for holding a magneto-optical material in accordance with yet a further embodiment of the present invention.
Figure 3H:
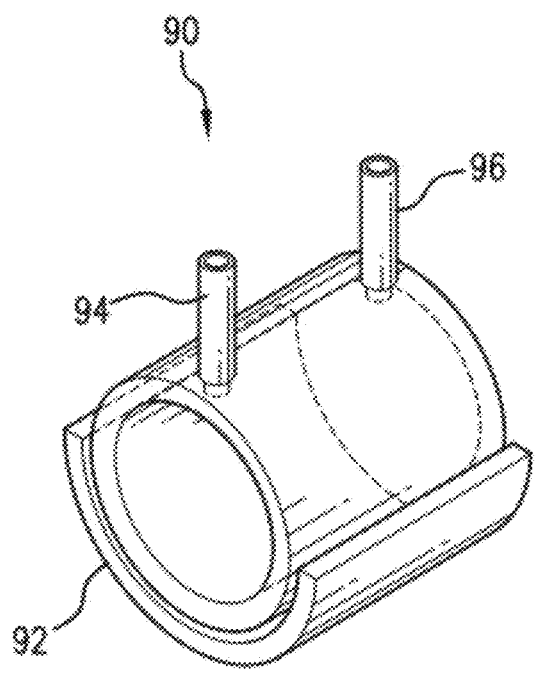
FIG. 3H is a perspective view of a sample holder comprising a heater/refrigerator and a device to hold a chemical in accordance with yet another embodiment of the present invention.

FIGS. 2D and 3H show system 10''' which is configured for chemical-optical property measurements, i.e. optical properties versus chemical concentration, chemical reaction, electro-chemical reaction, etc. System 10''' is configured to characterize numerous materials with advanced optical properties, phase, intensity, polarization, coherence, and etc. System 10' uses chemical sample holder 90. In one embodiment, sample holder 90 uses heater/refrigerator 92 in order to control temperatures. Sample holder 90 further comprises injection nozzle 94 and extraction nozzle 96. Chemicals are injected into sample holder 90 with injection and extraction nozzles 94 and 96, respectively. The chemical concentrations are controlled within sample holder 90. Chemical reactions are recorded with the dynamic change of the passing laser light's deep properties, such as phase, intensity, coherence, and polarization in time. In an alternate embodiment, an additional heater, refrigerator, or pressure cell is attached to sample holder 90.

Referring to FIGS. 3A, 3B and 3C, there are shown alternate types of electro-optic sample holders that can be utilized by system 10. In FIG. 3A, sample holder 100 comprises a pair of transparent electrodes 102 and 104. Electrode 102 is the positive electrode and electrode 104 is the negative electrode. Electro-optic material 106 is sandwiched between electrodes 102 and 104. Electro-optic material 106 may be in the form of thin-film, bulk, liquid, sol-gel, or solid form. During testing of electro-optical material 106, a voltage is applied to electrodes 102 and 104. Laser beam 108 passes through transparent electrodes 102 and 104. In one embodiment, electrodes 102 and 104 are fabricated from indium tin oxide components. Referring to FIGS. 3B and 3C, there is shown sample holder 150 which has the same general structure as sample holder 100. Sample holder 150 comprises a pair of transparent electrodes 152 and 154. Electrode 152 is the positive electrode and electrode 154 is the negative electrode. Electro-optic material 156 is sandwiched between electrodes 102 and 104. Electro-optic material 156 may be in the form of thin-film, bulk, liquid, sol-gel, or solid form. During testing of electro-optical material 106, a voltage is applied to electrodes 102 and 104. Laser beam 158 passes through transparent electrodes 152 and 154 such that the propagation direction of light is perpendicular to the direction of electric-field or current. Referring to FIG. 3D, there is shown sample holder 200 that is configured as a two dimensional array. Sample holder 200 allows system 10 to analyze multiple SOM cells simultaneously. The sample holders shown in FIGS. 3A, 3B and 3C can be configured with an array format.

Figure 9:
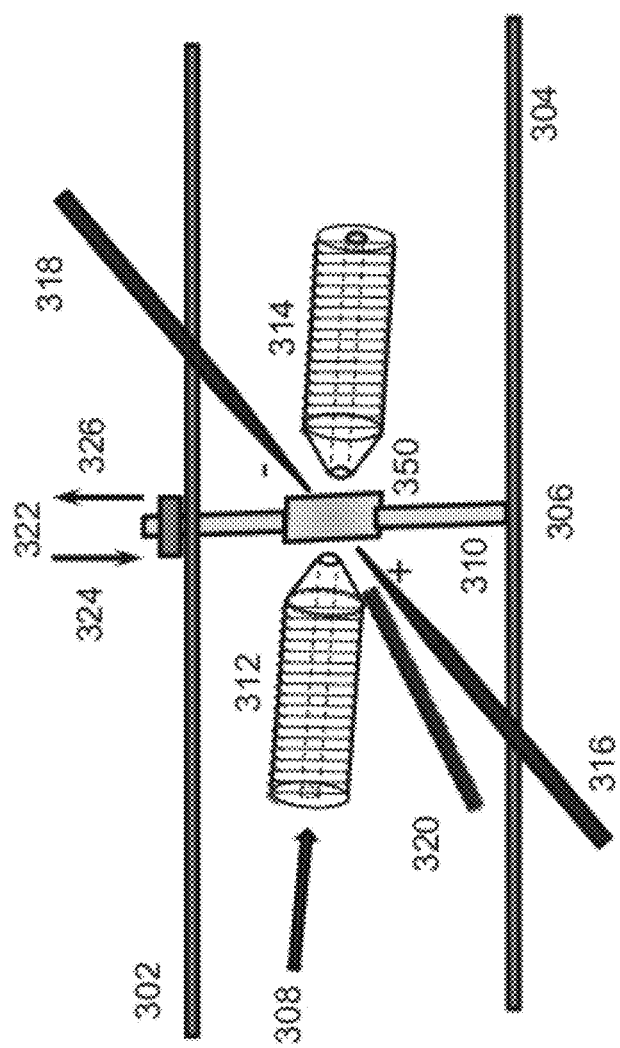
FIG. 9 shows a consolidated test platform for loading and subjecting a sample material to various physical quantities.

In at least one advantageous embodiment of the invention, the sample holders are combined into a consolidated test platform for applying multiple external influences such as electric, magnetic, thermal, and/or mechanical loads. An exemplary consolidated test platform 300 is shown in FIG. 9, where a sample 350 can be loaded and subjected to a selected field effect, electric, magnetic, thermal, or mechanical compression and tension for assaying the changes in optical characteristics. Such a test platform 300 includes housing components 302, 304 for rotational specimen holder 310 held by specimen support 306. Mechanical force 322 can be applied by compression means 324 or tension means 326. Test platform 300 allows either the application of a single field or even multiple fields simultaneously. In FIG. 9, electromagnetic pairs (312, 314) that face each other have a hole through the axial centerline for a probe beam 308 to pass through. The magnetic strength to the specimen on a test platform is controlled by the external power supply (not shown) for the electromagnet (312, 314). The electric field is provided by two electrodes (316, 318) that are beneficially aligned very close to the front and back surfaces of the sample 350 specimen. The electric field strength is controlled by the power supply (not shown) to the electrodes (316, 318). The incident angle of either magnetic or electric field is an important factor for determining the response along with the dipole orientation of the smart optical material in a specific direction and can be changed by the rotational specimen holder 310 which can be pivoted on the bottom floor 306 and top cap 322 of the instrument housing (302, 304) for rotational purposes. The sample 350 sitting on a specimen holder 310 can be grabbed by two mechanical grips (not shown) at the top and bottom in order to determine the mechanical compression (324), tension (326), and shear effects on the smart optical material. To create a shear effect on a specimen, the specimen grabber (not shown) that is attached to the top cap 322 rotates while the specimen support anchored on the housing floor 306 is fixed. Moreover, to see a thermal effect, the test platform encompasses a thermal gun 320 that can inject an infrared beam to the sample 350 specimen for determining thermal loading effect. The inventors believe that such a consolidated test platform can be installed within the compartment of the instant invention's interferometry system, with power supplies being advantageously placed outside the housing of such interferometry system.

Figure 4A:
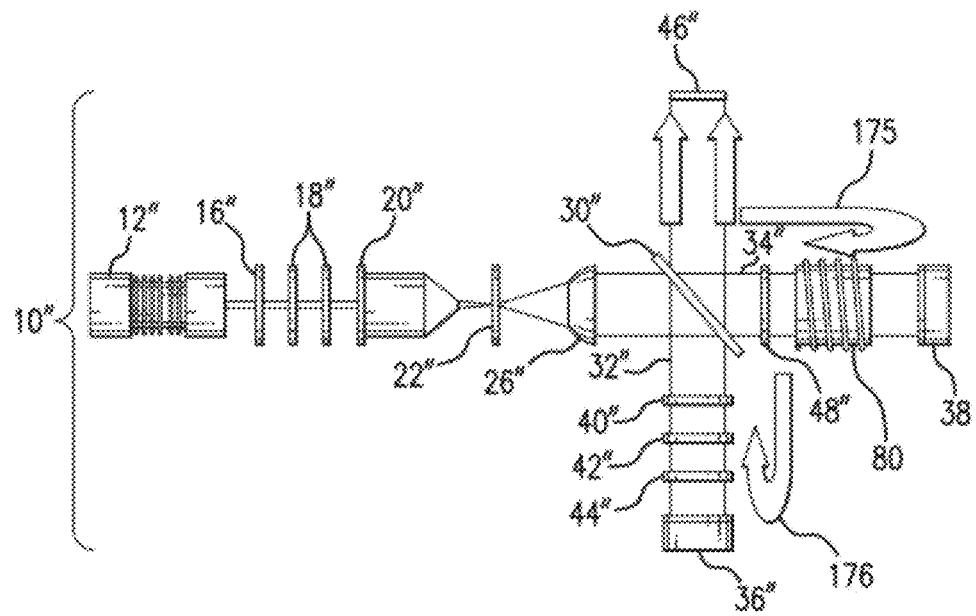
FIG. 4A is a diagram illustrating a roundtrip, double-pass-reflection configuration.

As described above, a system of the present invention can be configured to implement roundtrip, double-pass beam measurement. As shown in FIG. 1, system 10 is configured to implement roundtrip, double-pass beam measurement. Another example is system 10" which is shown in FIG. 4A. Beam 34" passes through the sample optical material in sample holder 80 twice, once in the forward direction and once in the backward or reverse direction as indicated by arrow 175 in FIG. 4A. The fact that beam 34" passes through the sample of optical material twice improves the accuracy of the measurement by a factor of two. Beam 32" is also reflected by mirror 36" and travels back through beam splitter 30" as indicated by arrow 176.

Figure 4B:
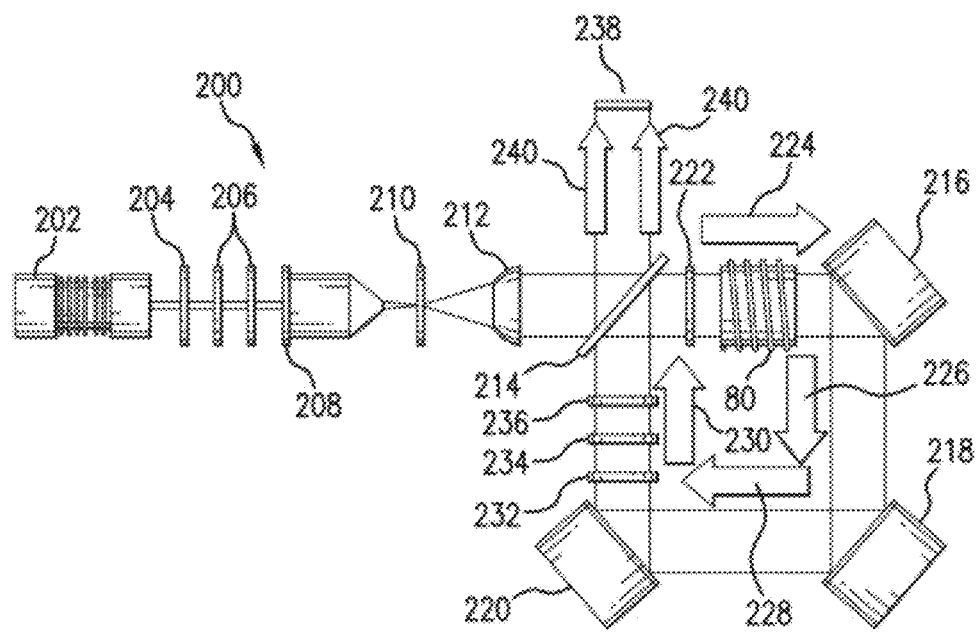
FIG. 4B is a diagram illustrating a unidirectional, single-pass-ring configuration.

The system of the present invention can also be configured in a unidirectional, single pass, beam path configuration. Such a configuration is necessary because characterization of some optical materials require a unidirectional, single pass, beam path. For example, Faraday rotator material under a magnetic field rotates the polarization of light by +45 degrees in a forward beam and −45 degrees in a backward beam along a magnetic field direction producing a total of 90 degrees rotation. If a user wants to measure a sample with a single beam pass configuration, the system of the present invention can be configured as shown by system 200 in FIG. 4B. System 200 comprises laser 202, polarizer 204, wave plates 206, neutral density filter 208, spatial filter 210 and plano-convex (PCX) lens 212 which provide the same function as like components discussed in the foregoing description with respect to system 10. System 200 further comprises beam splitter 214 and mirrors 216, 218 and 220. Mirrors 216, 218 and 220 are arranged as 45 degree angle mirrors. The laser light beam travels through beam splitter 214, through polarizer 222 and optical material in sample holder 80 as indicated by arrow 224. The laser light beam is then reflected at a 45 degree angle by mirror 216 as indicated by arrow 226. The laser light beam is then reflected at a 45 degree angle by mirror 218 as indicated by arrow 228. The laser light beam is then reflected by mirror 220 as indicated by arrow 230. The laser light beam then passes through optical components 232, 234 and 236, such as a polarizer, wave plate and/or neutral density filter. The laser light beam is then directed to imaging sensor 238 by beam splitter 214 as indicated by arrows 240. Imaging sensor 238 functions in the same manner as imaging sensor 46 (see FIG. 1). A processing resource (not shown) similar to processing resource 60 is in optical signal communication with imaging sensor 238.

In all of the embodiments described in the foregoing description, the beam splitters, mirrors and filters are interchangeable parts. The splitting ratio of the beam splitter depends upon measurement necessities and may be, for example and without limitation, ratios such as 50:50, 10:90, 30:70, 60:40, or 80:20.

The system of the present invention can use any one of several interference pattern recording configurations. One interference pattern recording configuration is direct recording on the imaging detector. In this configuration, a detector is used to record the interference pattern directly with or without an attenuator or screen. Another interference pattern recording configuration is an equally angled ($\theta_1 = \theta_2$) screen and camera module. In this configuration, the angle ($\theta_1$) between the normal vector of the screen and incoming interference pattern beam is the same as the angle ($\theta_2$) between the camera module and normal vector of screen such that distortion of interference pattern by angle $\theta_1$ is automatically corrected by the angle $\theta_2$ of the camera. A further interference pattern recording configuration is recording at an oblique angle. In this recording configuration, the camera module is at oblique angle $\theta_3$ and it has to be numerically corrected in the software of processing resource 60. The various embodiments of the characterizing systems described in the foregoing description may use any of these three recording configurations.

The present invention provides multi-functional and multi-conditional capabilities for any given optical system and thus, consolidates and covers all characterization processes into a single event job by a single system. Since the present invention improves precise control of phase and polarization of passing lights through Smart Optical Materials, the present invention has many applications including, but not limited to, phase-shift lithography, 3D stereo displays, holography and digital holographic displays, phase contrast microscopy, interferometers, waveguide modulators for fiber optical communication, vibrato-meters, adaptive telescopes, LIDAR, optical data storage, medical and pharmaceutical instruments, and the chemical industry. Other applications to which the present invention may be applied include refractive indices (static and real-time measurements under the varying electric field), spectral shift (static and real-time measurements under the varying electric field), and optical coatings (spectral uniformity based on optical surface and coating thickness), and measurement of the Stark effect, Zeeman effect, Faraday effect and Kerr effect. Other applications of the present invention include the characterization of non-linear optical materials, liquid crystals, electro-optic polymers, magneto-optic materials, and chromic materials. Further applications of the present invention include the measurement of absorption, reflection, transmission, polarization, intensity, phase, wavelength, and coherence.

The following example further illustrates the invention but, of course, should not be construed as in any way limiting its scope.

Example

Figure 5A:
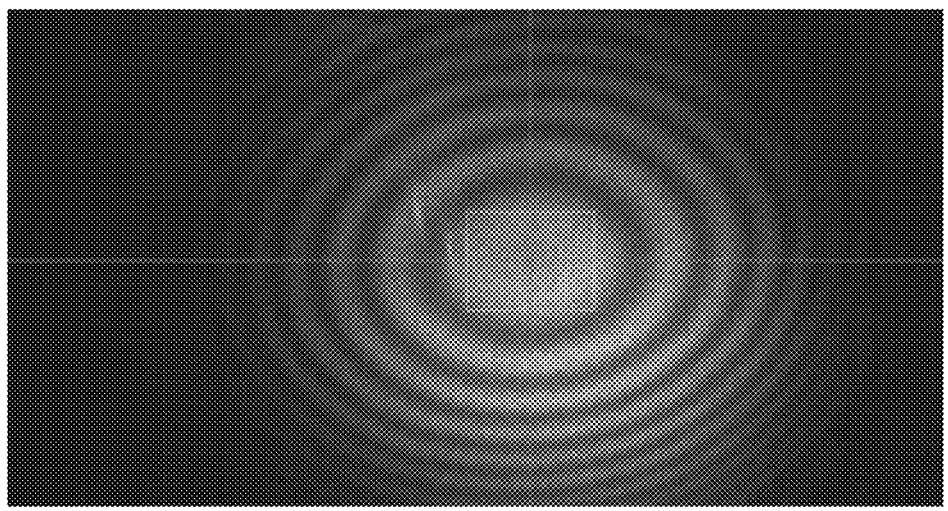
FIGS. 5A, 5B, 5C and 5D show data measured by the system of the present invention for a single layer liquid crystal cell.
Figure 5B:
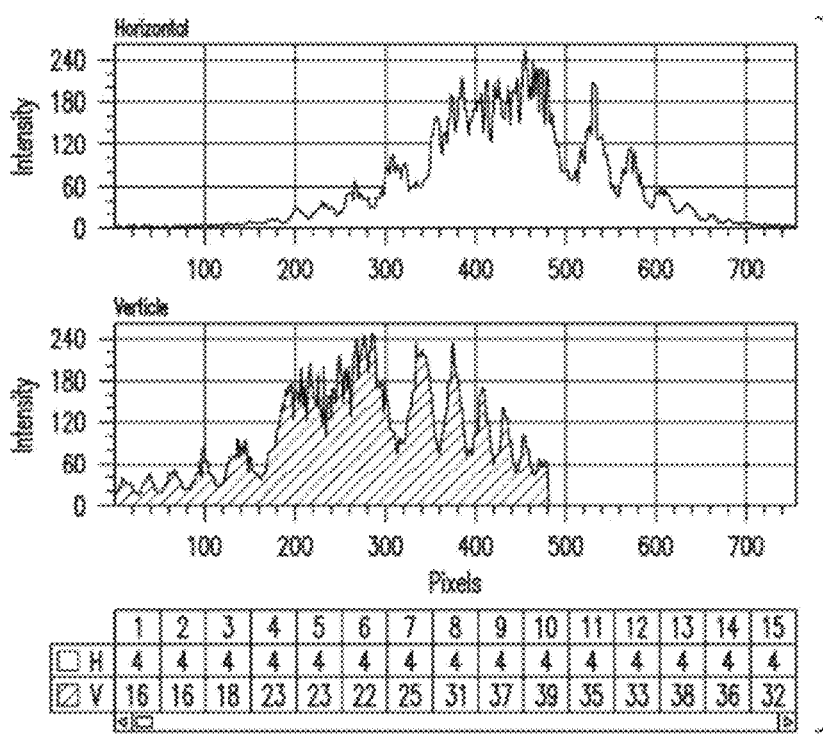
Figure 5C:
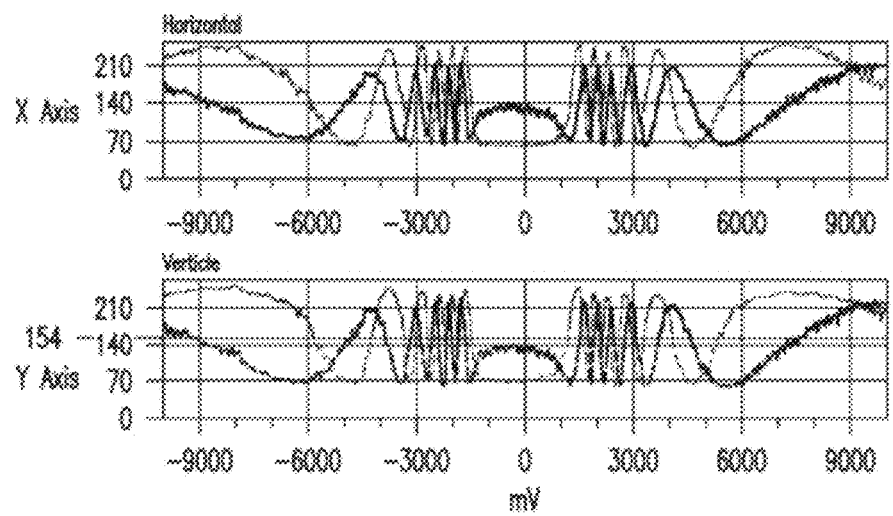
Figure 5D:
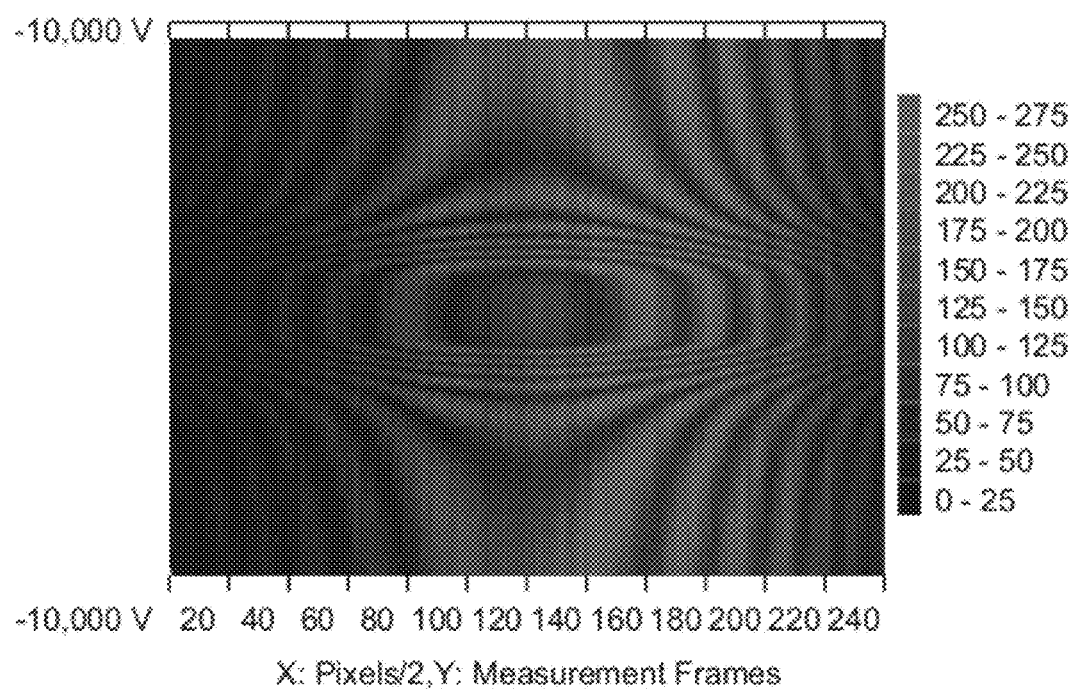

This example demonstrates a test measurement in accord with at least one embodiment of the invention, The test measurement was made with a transparent liquid crystal phase retarder. The liquid crystal layer was inserted between two transparent electrode layers and voltages from −10V to +10V were applied. FIGS. 5A, 5B, 5C and 5D show the data, measured by system 10, with a single layer of liquid crystal cell. System 10 provided a real-time display of the interference pattern, which is shown in FIG. 5A. Referring to FIG. 5A, a reference analysis zone was chosen by a user and displayed as a rectangle at the center of interference ripple with a horizontal line and vertical line. FIG. 5B is a graph showing real-time pixel intensity data from the horizontal line and vertical line shown in FIG. 5A. The user set the starting and ending voltages of a linear voltage scan-window and input the number of measurements, initial and step delay time. While applying voltages or currents to the sample of optical material, the processing resource 60 collected real-time data from the interference pattern provided by imaging sensor 46. FIG. 5C is a point intensity chart and shows collected data from the center of the interference ripple shown in FIG. 5A. As shown in FIG. 5C, sequential line intensity profiles on the vertical and horizontal lines of FIG. 5A were collected as system 10 applied various physical quantities on the optical material in time. The dynamic changes of this one-dimensional intensity profile (X-axis) were plotted with Y-axis as time or applied physical quantity, making a two-dimensional contour map shown in FIG. 5D. This contour map is referred to as a Phase Intensity Time Ripple Map (or Dynamic Photon Intensity Phase Map) since it recorded dynamic change of photon phase and intensity information with variation of applied physical/chemical quantities in time. In the real-time interference pattern display window, it appeared as though concentric ripples were disappearing into the center or generating out of the center depending on whether the refractive index was increasing or decreasing under applied physical/chemical quantities in time.

System 10 also provided the same type of data for a double layer of a liquid crystal cell. FIGS. 6A and 6B provide a comparison of data for single and double layers of liquid crystal cell. FIG. 6A pertains to a single layer of liquid crystal cell. FIG. 6B pertains to a double layer of liquid crystal cell. In FIG. 6A and FIG. 6B, the upper contour map was known as a Phase Intensity Time Ripple Map (also known as a Dynamic Photon Intensity Phase Map), and the lower graph was a point intensity measurement graph. Double layers of liquid crystal cells generated twice as many phase intensity changes than that of a single layer liquid crystal cell. The present invention not only measured dynamic change of just one point but also of the whole line. The vertical cross-section of the Phase Intensity Time Ripple Map showed dynamic change of photon intensity at one pixel. In FIG. 6A, line 300 in the point intensity chart shows dynamic photon intensity change at center point (cross-point of horizontal and vertical lines) and line 302 shows that of a side-reference point. Similarly, in FIG. 6B, line 304 in the point intensity chart shows dynamic photon intensity change at center point (cross-point of horizontal and vertical lines) and line 306 shows that of a side-reference point.

Referring to FIG. 7, there is shown the phase measurement result of the point intensity chart corresponding to the liquid crystal single layer (see FIG. 6A). The intensity is maximized at the phase angles of 0°, 360°, 720° and so on from the center while it is minimized at the phase angles of 180°, 540°, 900° and so on. The absolute phase angle changes were determined by measuring the maximum and minimum points of photon intensities with respect to the reference point's intensity changes. Intermediate phase angle values were measured as interpolation of photon intensities with respect to a reference point's photon intensity change. For instance, the middle point with zero bias voltage (0V) has 160 mV of photon intensity and maximum photon intensity of 200 mV between 0° phase angle points. Thus, this made absolute the phase angle change of cos-1 (160 mV/200 mV)=36.8°.

Figure 8:
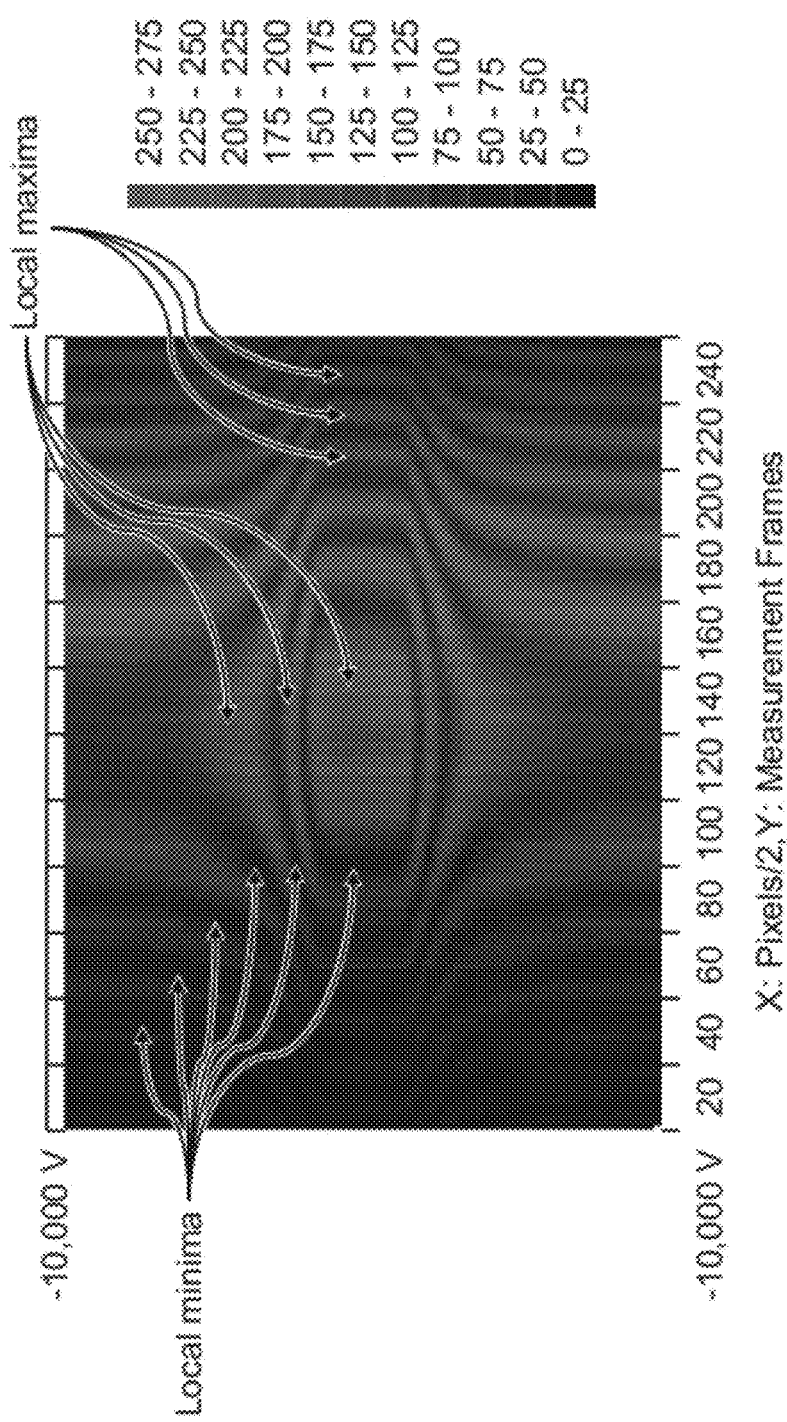
FIG. 8 shows a multi pixel phase measurement from a phase intensity time ripple map.

Referring to FIG. 8, there is shown a multi-pixel phase measurement derived from a phase intensity time ripple map. Processing resource 60 located the local maxima and minima region in the phase intensity time ripple map. In one embodiment, numerical calculation with simulated annealing was used to find local maxima regions for phase angle differences of 0°, 360°, 720° and so on. Similarly, another numerical calculation with simulated annealing was used to locate local minima regions for phase angle differences of 180°, 540°, 900° and so on. Based on these mathematical calculations, contour lines for maximum region and minimum region were located. Processing resource 60 calculated intermediate phase angles as interpolated equal-intensity contours between maxima and minima regions. Processing resource 60 calculated phase angles of whole lines instead of just a few points.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed as new and desired to be secured by Letters Patent of the United States is:

1. A method for characterizing optical materials, comprising the steps of:

providing a sample of optical material in a sample holder configured to grip a top and a bottom of the optical material;

applying tension, compression, shear, or torsional stress to the optical material via two housing grip components located on opposite ends of the sample holder;

generating a coherent laser light;

filtering the coherent laser light in order to remove high order spatial components of laser light;

collecting the filtered light and forming a parallel beam of light;

applying a magnetic field to the optical material without contacting via a first electromagnet and a second electromagnet, the first electromagnet and second electromagnet both having holes through their axially aligned center lines;

splitting the parallel beam of light into a first direction and into a second direction wherein the parallel beam of light travelling in the second direction travels toward the sample of optical material so that the parallel beam of light passes through the hole of the first electromagnet to pass through the optical material and then passes through the hole of the second electromagnet while the optical material is under mechanical stress of compression, tension, torsion, or shear forces;

applying an infrared beam to the optical material to increase and set a temperature of the optical material to a point of interest via a thermal gun;

applying an electric field to the optical material via two electrodes;

reflecting the beam of light travelling in the first direction to produce a first reflected beam of light;

reflecting the beam of light that passes through the optical material off a mirror separate from the optical material to produce a second reflected beam of light that travels back through the hole of the second electromagnet, then back through the optical material, and then back through the hole of the first electromagnet;

combining the second reflected beam of light after it travels back though the optical material with the first reflected beam of light;
sensing the light beam produced by combining the first and second reflected beams of light; and
processing the sensed light beam to determine the optical characteristics and properties of the sample of optical material by extracting phase angle changes of one or multiple two-dimensional images of the sensed light beam by computing relative intensity changes after determining and comparing a cardinal order of local minima and maxima of intensities of two or more points of the one or multiple two dimensional images as one or more of the shear, torsion, tension, compression, acoustic field, magnetic field, electric field, and infrared beam for thermal effect are applied.

2. The method according to claim 1 further comprising the steps of:
polarizing the generated coherent laser light; and
modifying the polarized coherent laser light.

3. The method according to claim 1 further comprising the step of attenuating the power of the coherent laser light to a predetermined power level.

4. The method according to claim 1 wherein the step of processing comprises detecting an interference pattern of the sensed light beam.

5. The method according to claim 4 wherein the step of processing further comprises the step of measuring the dynamic change of the interference pattern.

6. The method according to claim 5 wherein the step of processing further comprises the step of determining spectral and refractive index shifts in terms of intensity, phase, polarization and coherence of the light passing through the sample of optical material.

7. The method according to claim 1 further comprising the step of attenuating the power level of the first reflected light beam.

8. A system for characterizing optical materials, comprising:
a sample holder for holding a sample of optical material, wherein the sample holder is configured to twist the optical material;
two housing grip components located on opposite ends of the sample holder and configured to apply tension, compression, shear, or torsional stress to the optical material;
a laser to generate a coherent laser light;
a filter for filtering the coherent laser light in order to remove high order spatial components of laser light;
an optical device to collect the filtered light and forming a parallel beam of light;
a first electromagnet and a second electromagnet, the first electromagnet and second electromagnet both having holes aligned through their axial center lines and configured to apply a magnetic field to the optical material;
an optical beam splitter to split the parallel beam of light into a first direction and into a second direction, wherein the parallel beam of light travelling in the second direction travels toward the sample of optical material so that the parallel beam of light passes through the hole of the first electromagnet to pass through the sample of optical material secured within the sample holder and then passes through the hole of the second electromagnet;
a thermal gun configured to apply an infrared beam to the optical material to increase and to set a temperature at a designated point;
two electrodes configured to apply an electric field to the optical material;
a first optical reflector to reflect the beam of light travelling in the first direction to produce a first reflected beam of light;
a second optical reflector to reflect the beam of light that passes through the optical material to produce a second reflected beam of light that travels back through the hole of the second electromagnet, then back through the optical material, and then back through the hole of the first electromagnet, wherein the optical beam splitter is further configured to combine the second reflected beam of light after it travels back through the optical material with the first reflected beam of light, wherein the second optical reflector is a mirror separate from the optical material;
an imaging sensor to sense the light beam produces by combining the first and second reflected beams of light; and
a processing resource to process the sensed light beam to determine the optical characteristics and properties of the sample of optical material by extracting phase angle changes of one or multiple two-dimensional images of the sensed light beam by computing relative intensity changes after determining and comparing a cardinal order of local minima and maxima of intensities of two or more points of the one or multiple two dimensional images as one or more of the shear, torsion, tension, compression, magnetic field, electric field, and infrared beam are applied.

9. The system according to claim 8 wherein the filter comprises a spatial filter.

10. The system according to claim 8 wherein the optical device comprises a plano-convex lens.

11. The system according to claim 8 further comprising:
a polarizer to polarize the generated coherent laser light; and
a wave plate to alter the polarization of the polarized coherent laser light.

12. The system according to claim 8 further comprising a device to attenuate the power of the coherent laser light to a predetermined power level.

13. The system according to claim 12 wherein the device comprises a neutral density filter.

14. The system according to claim 8 wherein the imaging sensor comprises a detector to detect an interference pattern of the sensed light beam.

15. The system according to claim 14 wherein the processing resource includes processing means to process the interference pattern detected by the imaging sensor.

16. The system according to claim 15 wherein the processing resource comprises processing means to measure the dynamic change of the interference pattern.

17. The system according to claim 16 wherein the processing resource further comprises processing means to determine the spectral and refractive index shifts in terms of intensity, phase, polarization and coherence of the light passing through the sample of optical material.

18. The system according to claim 8 wherein the processing resource comprises a computer and a device to display the optical characteristics and properties of the optical material.

19. The system according to claim 8 further comprising a device to attenuate the power level of the first reflected light beam.

20. The system according to claim 8, wherein the system is miniaturized and comprises a USB type interface.

* * * * *